(12) United States Patent
Li et al.

(10) Patent No.: US 8,492,409 B2
(45) Date of Patent: Jul. 23, 2013

(54) 1-SUBSTITUTED PYRIDYL-PYRAZOLYL AMIDE COMPOUNDS AND USES THEREOF

(75) Inventors: Bin Li, Shenyang (CN); Huibin Yang, Shenyang (CN); Junfeng Wang, Shenyang (CN); Haibo Yu, Shenyang (CN); Hong Zhang, Shenyang (CN); Zhinian Li, Shenyang (CN); Yuquan Song, Shenyang (CN)

(73) Assignees: Sinochem Corporation, Beijing (CN); Shenyang Research Institute of Chemical Industry Co., Ltd., Shenyang, Liaoning (CN)

( * ) Notice: Subject to any disclaimer, the term of this patent is extended or adjusted under 35 U.S.C. 154(b) by 133 days.

(21) Appl. No.: 12/990,193

(22) PCT Filed: Jul. 3, 2009

(86) PCT No.: PCT/CN2009/072612
§ 371 (c)(1),
(2), (4) Date: Oct. 28, 2010

(87) PCT Pub. No.: WO2010/003350
PCT Pub. Date: Jan. 14, 2010

(65) Prior Publication Data
US 2011/0046186 A1 Feb. 24, 2011

(30) Foreign Application Priority Data
Jul. 7, 2008 (CN) .......................... 2008 1 0116198

(51) Int. Cl.
A01N 43/40 (2006.01)
C07D 401/04 (2006.01)

(52) U.S. Cl.
USPC .................. 514/340; 546/275.4; 546/276.1

(58) Field of Classification Search
USPC .................. 546/275.4, 276.1; 514/340
See application file for complete search history.

(56) References Cited

FOREIGN PATENT DOCUMENTS

| WO | 03015518 A1 | 2/2003 |
|---|---|---|
| WO | 2008010897 A2 | 1/2008 |
| WO | 2008/134970 | * 11/2008 |

* cited by examiner

*Primary Examiner* — Patricia L Morris
(74) *Attorney, Agent, or Firm* — Smith, Gambrell & Russell, LLP

(57) ABSTRACT

The present invention discloses a kind of 1-substituted pyridyl-pyrazolyl amide compounds and uses thereof. The compounds have structures as represented by the general formula I, wherein the definitions of each substituent showed in the specification. The compounds of formula I are novel and have excellent insecticidal and fungicidal activities and can be used for controlling insect pest and diseases.

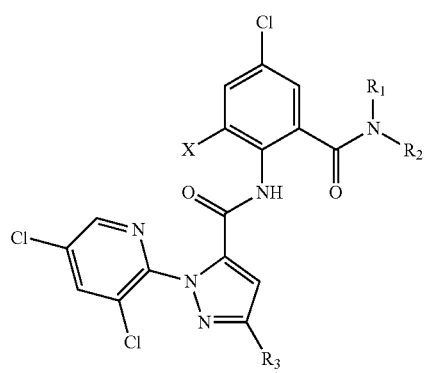

6 Claims, No Drawings

1-SUBSTITUTED PYRIDYL-PYRAZOLYL AMIDE COMPOUNDS AND USES THEREOF

FIELD OF THE INVENTION

The present invention belongs to the field of insecticide or fungicide, relates to a kind of 1-substituted pyridyl-pyrazolyl amide compounds and uses thereof.

BACKGROUND OF THE INVENTION

The search for novel and improved insecticidal or fungicidal compounds or compositions is continually needed because of the emergence and development of the insect or fungi resistance to the existing insecticides or fungicides after a period of applications. Simultaneously, with the growing demands for agricultural and animal products, as well as the awareness on the environmental protection, the cost-effective or environmentally friendly novel insecticides or fungicides are always needed.

The preparation and insecticidal activity of 1-(3-chloro-5-bromopyridin-2-yl)-pyrazole carboxamide compound ($KC_1$) was disclosed in US 2005/0075372 A1, which is highly effective against armyworm (*Mythimna seperata*) at 50 ppm. US 2005/0075372 A1 also disclosed the compound $KC_2$ which has highly effective against fall armyworm (*Spodoptera frugiperda*) at 10 ppm. $KC_2$ has been commercialized as an insectide, and its common name is chlorantraniliprole.

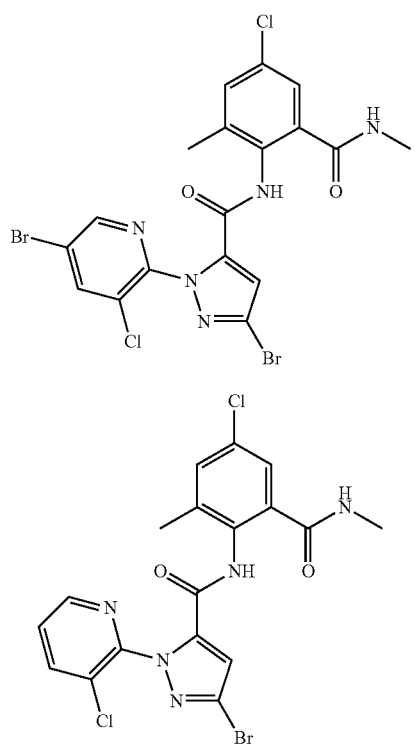

$KC_1$ $KC_2$

Neither the preparation of 1-(3,5-dichloropyridin-2-yl)-pyrazolyl carboxamide compounds, nor their insecticidal or fungicidal activities according to the present invention are described in state of the arts.

SUMMARY OF THE INVENTION

The purpose of the present invention is to provide a kind of novel 1-substituted pyridyl-pyrazolyl amide compounds, and their applications for controlling insect or disease in agriculture, forestry or public health.

The technical embodiments of this invention are as follows:

A kind of 1-substituted pyridyl-pyrazolyl amide compounds as represented by the general formula I:

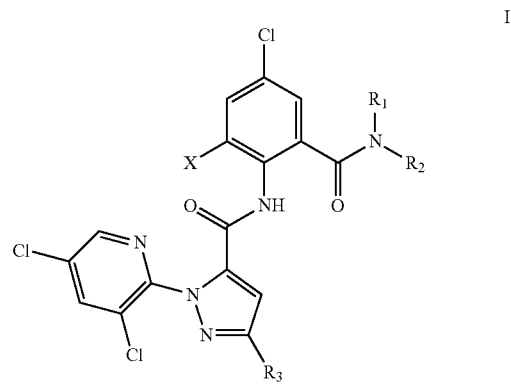

I

Wherein:
$R_1$ is H or $C_1$-$C_3$ alkyl;
$R_2$ is H, $C_1$-$C_6$ alkyl, $C_3$-$C_6$ alkenyl, $C_3$-$C_6$ alkynyl or $C_3$-$C_6$ cycloalkyl;
$R_3$ is Cl, Br, $CH_3$, $CF_3$, $C_1$-$C_3$ alkoxy, $C_1$-$C_3$ haloalkoxy, $C_2$-$C_6$ cyanoalkoxy, $C_3$-$C_6$ alkenyloxy or $C_3$-$C_6$ alkynyloxy;
X is F, Cl, Br or $CH_3$.

The preferred compounds of the general formula I in the present invention are:
$R_1$ is H;
$R_2$ is H, $C_1$-$C_6$ alkyl or $C_3$-$C_6$ cycloalkyl;
$R_3$ is Cl, Br, $CH_3$, $CF_3$, methoxy, trifluoromethoxy, cyanomethoxy, propenyloxy or propynyloxy;
X is $C_1$ or $CH_3$.

Taking the convenient synthesis, preparation cost, environmentally friendliness and other factors into account the more preferred compounds of the general formula I in the invention are:
$R_1$ is H;
$R_2$ is H or $CH_3$;
$R_3$ is Cl or Br;
X is $C_1$ or $CH_3$.

In above definitions of the compounds of general formula I, the term "alkyl" indicates straight-chain or branched alkyl such as methyl, ethyl, n-propyl, i-propyl, n-butyl, i-butyl, s-butyl, t-butyl, n-pentyl, i-pentyl, n-hexyl, etc. "Cycloalkyl" indicates cyclo-chain forms such as cyclopropyl, methylcyclopropyl, cyclopropylcyclopropyl, cyclobutyl, cyclopentyl and cyclohexyl, etc. "Alkenyl" indicates straight-chain or branched alkenes such as 1-propenyl, 2-propenyl, butenyl, pentenyl and hexynyl, etc. "Alkynyl" includes straight-chain or branched alkynes such as 1-propynyl, 2-propynyl, butynyl, pentynyl, hexynyl, etc. "Alkoxy" is that the end of alkyl is oxygen, such as methoxy, ethoxy, n-propyloxy, i-propyloxy, t-butoxy, etc. "Haloalykoxy" is that the end of the alkyl substituted with one or more halogen atoms is oxygen. "Cyanoalkoxy" is that the end of the alkyl substituted with one or more cyano atoms is oxygen. "Alkenyloxy" is that the end of alkenyl is oxygen. "Alkynyloxy" is that the end of alkynyl is oxygen.

The compounds of general formula I in the present invention can be prepared by the following two methods, and the substituents in the reaction schemes are same as above definitions:

Method I:

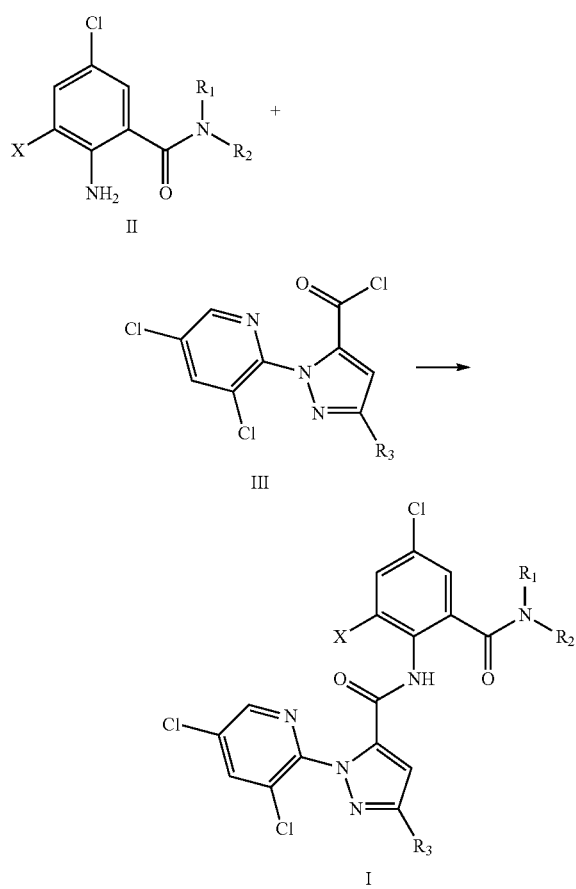

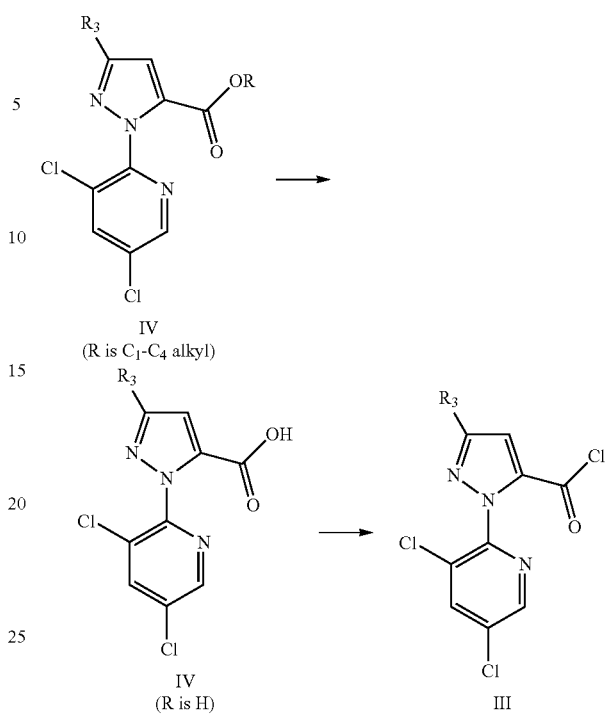

The compounds of general formula II and III are reacted in an appropriate solvent to yield the compounds of general formula I at a certain temperature from −10° C. to boiling point for 30 minutes to 48 hours.

The appropriate solvent is selected from dichloromethane, chloroform, carbon tetrachloride, hexane, benzene, toluene, ethyl acetate, acetonitrile, tetrahydrofuran, dioxane, N,N-dimethylformamide or dimethyl sulfoxide etc.

The appropriate base is advantageous to the reaction. The appropriate base is selected from organic base such as triethylamine, N,N-dimethylaniline or pyridine, etc., or inorganic base such as sodium hydroxide, potassium hydroxide, sodium methoxide, sodium tert-butoxide or potassium tert-butoxide, etc.

The compounds of general formula II can be prepared according to the procedures disclosed in the US2006/079561A1.

The compounds of general formula III can be prepared by the following processes:

The carboxylic acid ester compounds of above general formula IV (When R is $C_1$-$C_4$ alkyl) can be hydrolysised to form the carboxylic acid compounds of general formula IV (R is H) under basic conditions. (See T. W. Greene and P. G. M. Wuts, Protecting groups in organic synthesis, 2nd ed. John Wiley & Sons, Inc., New York, 1991, pp. 224-269: review of the methods). The appropriate bases are selected from alkali metals hydroxide such as alkali metals of lithium, sodium or potassium.

Carboxylic acid compounds (R is H in compounds of general formula IV) and acyl halide reagents are reacted in an appropriate solvent to yield the compounds of general formula III at a certain temperature from −10° C. to boiling point for 30 minutes to 48 hours. The appropriate acyl halide reagent is selected form oxalyl chloride, thionyl chloride, phosphorus trichloride, phosphorus tribromide, phosphorus pentachloride or phosphorus pentabromide, and the mole ratio of carboxylic acid to acyl halide reagents is 1:1-20. The appropriate solvent is selected from dichloromethane, hexane, benzene, toluene, acetonitrile, dioxane or liquid acyl halide reagents.

The compounds of general formula IV can be prepared by the following three processes:

(1) Keto Esters Method:

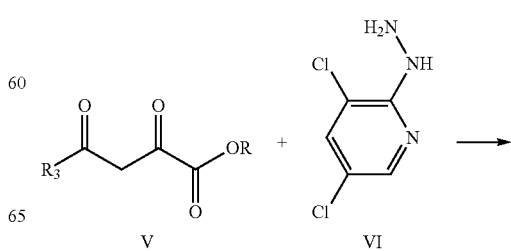

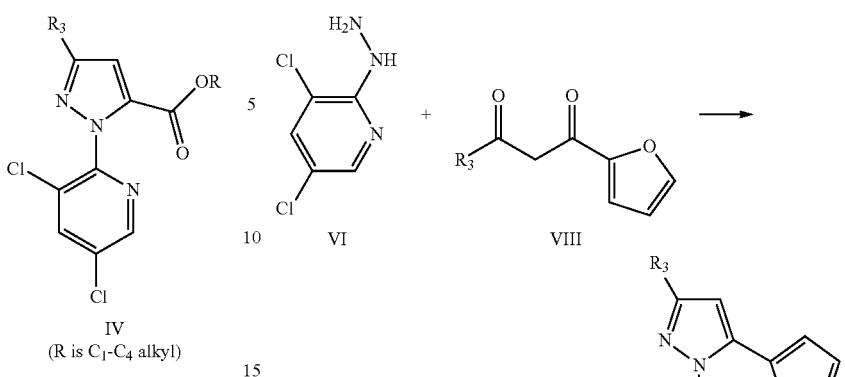

IV
(R is C$_1$-C$_4$ alkyl)

The compounds of general formula V and the compounds of general formula VI are reacted in an appropriate solvent to yield the compounds of general formula IV at a certain temperature from 0° C. to boiling point for 30 minutes to 48 hours. The appropriate solvent is selected from methanol, ethanol, benzene, toluene, acetonitrile, dioxane, tetrahydrofuran or acetic acid.

The compounds of general formula V can be prepared by ketone reacted with oxalate ester in an appropriate solvent under basic conditions at a certain temperature from 10° C. to boiling point for 30 minutes to 48 hours. The appropriate base is selected from alkaline metal alkoxide such as sodium methoxide, potassium methoxide, sodium ethoxide, potassium ethoxide, sodium tert-butoxide, or potassium tert-butoxide etc. The appropriate solvent is selected from methanol, ethanol, benzene, toluene, acetonitrile, dioxane or tetrahydrofuran. Corresponding ketones and oxalate esters are commercially available.

The compounds of general formula VI can be prepared by corresponding halogenated pyridine reacted with hydrazine in an appropriate solvent. The appropriate solvent is selected from methanol, ethanol, benzene, toluene, acetonitrile, dioxane or tetrahydrofuran. The corresponding halogenated pyridine is commercially available.

(2) Diketone Method

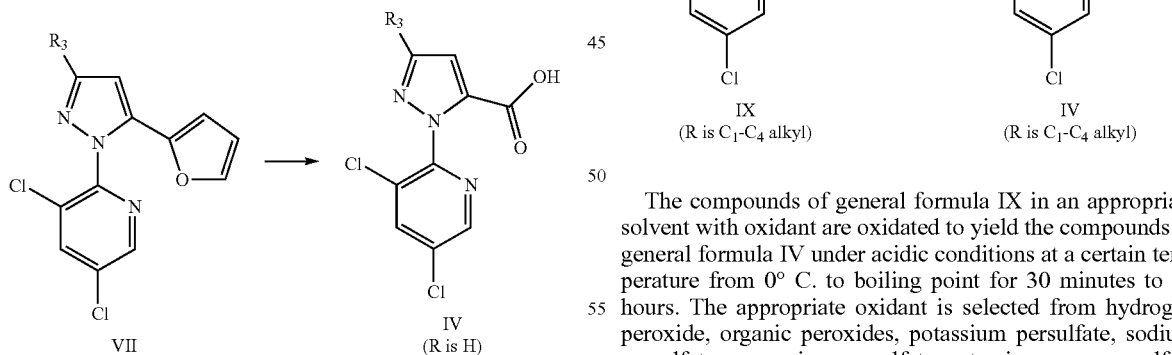

The compounds of general formula VII in the solvent with appropriate oxidant is oxidized to form the carboxylic acid compounds of general formula IV (R is H). The appropriate oxidant is selected from hydrogen peroxide, organic peroxides, potassium persulfate, sodium persulfate, ammonium persulfate, potassium monopersulfate or potassium permanganate. The appropriate solvent is selected from, water, acetone, tetrahydrofuran, dioxane, ethyl acetate, N,N-dimethylformamide or acetonitrile, etc.

The compounds of general formula VI and the compounds of general formula VIII are reacted in the solvent to yield the compounds of general formula VII at a certain temperature from 0° C. to boiling point for 30 minutes to 48 hours. The appropriate solvent is selected from methanol, ethanol, benzene, toluene, acetonitrile, dioxane, tetrahydrofuran or acetic acid. The corresponding alkyl acyl furans are commercially available.

(3) Alkenylcarboxylic Ester Method

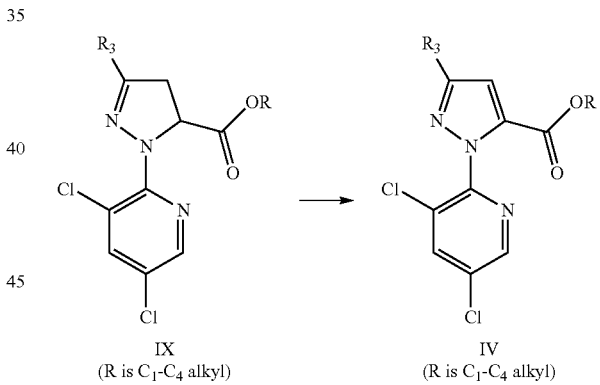

IX
(R is C$_1$-C$_4$ alkyl)

IV
(R is C$_1$-C$_4$ alkyl)

The compounds of general formula IX in an appropriate solvent with oxidant are oxidated to yield the compounds of general formula IV under acidic conditions at a certain temperature from 0° C. to boiling point for 30 minutes to 48 hours. The appropriate oxidant is selected from hydrogen peroxide, organic peroxides, potassium persulfate, sodium persulfate, ammonium persulfate, potassium monopersulfate or potassium permanganate. The appropriate solvent is selected from tetrahydrofuran, dioxane, ethyl acetate, N,N-dimethylformamide, acetonitrile etc. The appropriate acid used in the oxidation step is selected from sulfuric acid, phosphoric acid or acetic acid etc.

The compounds of general formula IV when R$_3$ is substituted oxygen group can be obtained in an appropriate solvent by the reaction of the compounds of general formula IV (R$_3$ is hydroxyl) with halides at a certain temperature from −10° C. to boiling point for 30 minutes to 48 hours. The appropriate solvent is selected from dichloromethane, chloroform, carbon tetrachloride. N,N-dimethylformamide, tetrahydrofuran, acetonitrile, dioxane or DMSO, etc. The appropriate halides such as iodomethane, allyl bromide or propargyl bromide etc. are commercially available.

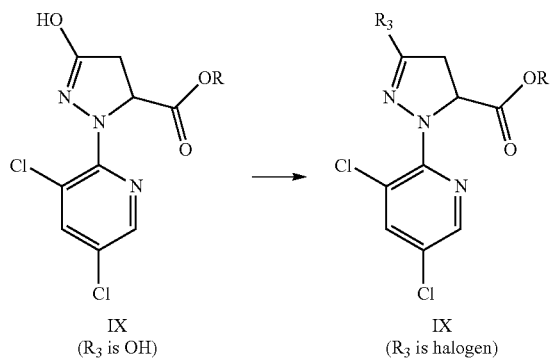

IX
(R₃ is OH)

IX
(R₃ is halogen)

The compounds of general formula IX (R₃ is OH) in an appropriate solvent react with halogenating agent at a certain temperature from −10° C. to boiling point for 30 minutes to 48 hours, and the reaction mixture is neutralized with base to get the corresponding compounds of general formula IX (R₃ is halogen). The appropriate halogenating agent is selected from phosphorus oxyhalides, phosphorus trihalides, phosphorus pentahalides, thionyl chloride, dihalotrialkylphosphoranes, dihalodiphenylphosphoranes, oxalyl chloride or carbonyl chloride. The appropriate solvent is selected from dichloromethane, chloroform, chlorobutane, benzene, xylene, chlorobenzene, tetrahydrofuran, dioxane, ethyl ether, acetonitrile, N,N-dimethylformamide etc. The appropriate base is selected from inorganic base such as sodium bicarbonate, sodium hydroxide, etc., or organic base such as sodium acetate.

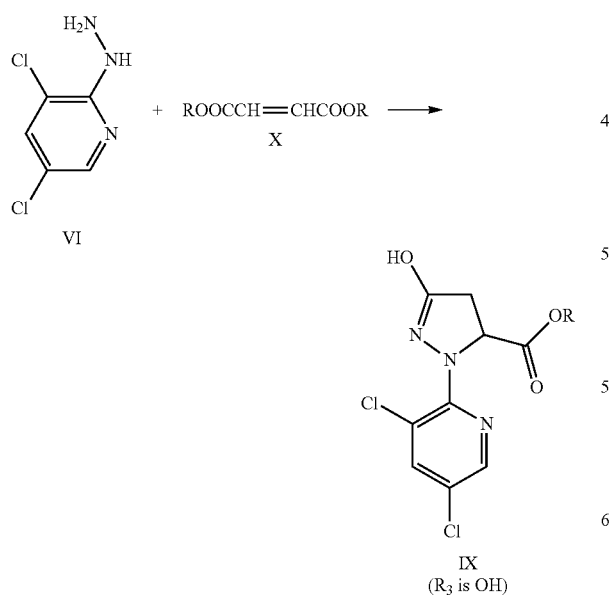

The compounds of general formula VI react with the compounds of general formula X (Such as fumarate or maleate, or their mixture), then acidified with the appropriate acid to yield the compounds of general formula IX in the presence of appropriate solvent and base at a certain temperature from −10° C. to boiling point for 30 minutes to 48 hours. The appropriate base is selected from alkali metal alkoxide such as sodium methoxide, potassium methoxide, sodium ethoxide, potassium ethoxide, sodium tert-butoxide or potassium tert-butoxide, ect. The appropriate solvent is selected from alcohols such as ethanol or methanol. The appropriate acid is selected from organic acids such as acetic acid, etc., or inorganic acids such as hydrochloric acid, or sulfuric acid, etc. The compounds of general formula X such as maleate, etc., are commercially available.

Method II:

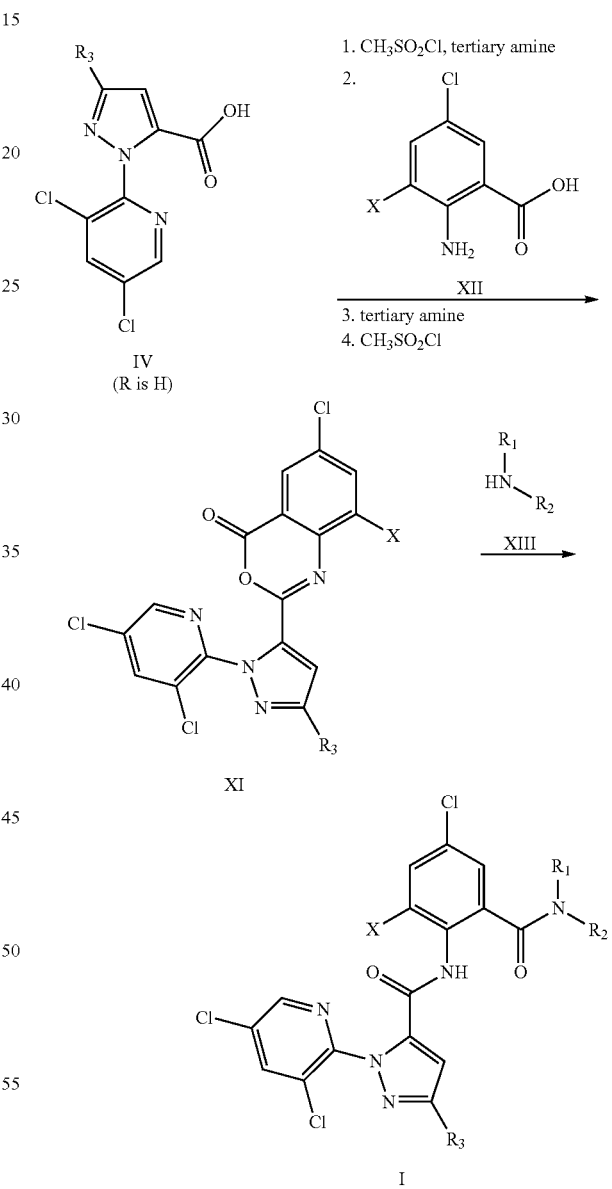

Benzoxazinone XI can be prepared by the following processes:

To add a solution of methanesulfonyl chloride into an appropriate solvent and then added sequentially the mixture of the compounds of general formula IV (R is H) and tertiary amine, and anthranilic acid XII. Then tertiary amine and methanesulfonyl chloride are added to the mixture to get the compounds of general formula XI. The appropriate solvent is selected from chlorobenzene, toluene, ethyl acetate, butyl acetate, acetone, 2-butanone, tetrahydrofuran, dioxane, acetonitrile, dichloromethane or chloroform. The anthranilic acids of general formula XII can be prepared according to the method disclosed in US2005075372. The tertiary amine is selected from triethylamine or tributylamine, etc.

The amines XIII react with the benzoxazinone XI in an appropriate solvent to yield the title compounds of general formula I at a certain temperature from 0° C. to boiling point for 30 minutes to 48 hours. The appropriate solvent is selected from tetrahydrofuran, diethyl ether, pyridine, dichloromethane or chloroform, etc. The reactions of the benzoxazinone XI with the amines XIII to obtain the anthranilamides are fully disclosed in chemical literature. (See *Biorganic and Medicinal Chemistry* 2000, 8, 2095-2103; and *J. Heterocyclic Chemistry,* 1999, 36, 563-588.) The corresponding amines are commercially available.

The table 1 shows the structures and their physical properties of some representative compounds of general formula I:

TABLE 1

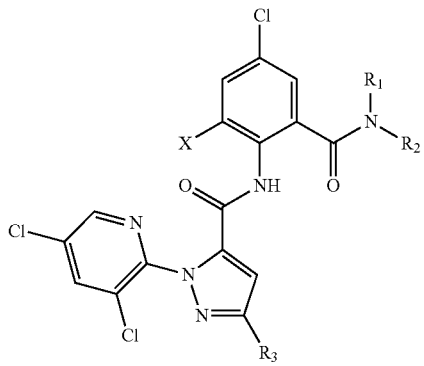

| Compound | $R_1$ | $R_2$ | $R_3$ | X | Appearance (m.p.(° C.)) |
|---|---|---|---|---|---|
| 1 | H | $CH_3$ | $CH_3$ | $CH_3$ | white solid(196-198) |
| 2 | $CH_3$ | $CH_3$ | $CH_3$ | $CH_3$ | white solid(197-200) |
| 3 | H | $CH_3$ | $CF_3$ | $CH_3$ | white solid(213-216) |
| 4 | H | $CH_3$ | $OCH_3$ | $CH_3$ | white solid(120-122) |
| 5 | H | $CH_3$ | $OCH_2CF_3$ | $CH_3$ | |
| 6 | H | $CH_3$ | $OCH_2CN$ | $CH_3$ | |
| 7 | H | $CH_3$ | $OCF_2CF_3$ | $CH_3$ | |
| 8 | H | $CH_3$ | $OCH_2CH=CH_2$ | $CH_3$ | white solid(205-208) |
| 9 | H | $CH_3$ | $OCH_2C\equiv CH$ | $CH_3$ | white solid(171-174) |
| 10 | H | $CH_3$ | Cl | $CH_3$ | white solid(206-209) |
| 11 | H | $CH_3$ | Cl | Cl | white solid(155-157) |
| 12 | H | $CH_3$ | Cl | Br | |
| 13 | H | $CH_3$ | Cl | F | |
| 14 | H | H | Br | Cl | white solid(240-243) |
| 15 | H | H | Br | $CH_3$ | white solid(253-255) |
| 16 | H | H | Cl | Cl | white solid(237-240) |
| 17 | H | H | Cl | $CH_3$ | white solid(245-248) |
| 18 | H | $CH_3$ | Br | $CH_3$ | white solid(135-138) |
| 19 | H | $CH_3$ | Br | Cl | white solid(175-178) |
| 20 | H | $CH_3$ | Br | Br | |
| 21 | H | $CH_3$ | Br | F | |
| 22 | H | —$CH_2CH_3$ | Br | $CH_3$ | white solid(221-225) |
| 23 | H | —$CH(CH_3)_2$ | Br | $CH_3$ | white solid(223-225) |
| 24 | H | cyclopropyl | Br | $CH_3$ | white solid(228-231) |
| 25 | H | cyclohexyl | Br | $CH_3$ | white solid(238-241) |
| 26 | H | —$CH_2C\equiv CH$ | Br | $CH_3$ | white solid(126-129) |

Compounds $^1$H NMR (300 MHz, CDCl$_3$) data as follows:

Compound 1: 9.979 (br s, 1H), 8.393 (d, 1H), 7.833 (d, 1H), 7.220-7.178 (m, 2H), 6.911 (s, 1H), 6.234 (br s, 1H), 2.922 (d, 3H), 2.420 (s, 3H), 2.176 (s, 3H).

Compound 2: 10.001 (br s, 1H), 8.383 (d, 1H), 7.808 (d, 1H), 7.126 (s, 1H), 7.033-6.931 (m, 2H), 3.061 (s, 3H), 2.754 (s, 3H), 2.403 (s, 3H), 2.018 (s, 3H).

Compound 3: 10.384 (br s, 1H), 8.400 (d, 1H), 7.877 (d, 1H), 7.642 (s, 1H), 7.099-7.074 (m, 2H), 6.269 (br s, 1H), 2.894 (d, 3H), 2.077 (s, 3H).

Compound 4: 9.986 (br s, 1H), 8.371 (d, 1H), 7.812 (d, 1H), 7.077-7.065 (m, 2H), 6.636 (s, 1H), 6.455 (br d, 1H), 3.987 (s, 3H), 2.857 (d, 3H), 2.083 (s, 3H).

Compound 8: 9.996 (br s, 1H), 8.368 (d, 1H), 7.817 (d, 1H), 7.120-7.100 (m, 2H), 6.637 (s, 1H), 6.357 (br s, 1H), 6.140-6.047 (m, 1H), 5.467-5.276 (m, 2H), 4.790 (d, 2H), 2.879 (d, 3H), 2.111 (s, 3H).

Compound 9: 10.012 (br s, 1H), 8.375 (d, 1H), 7.824 (d, 1H), 7.266-7.163 (m, 2H), 6.627 (s, 1H), 6.208 (br s, 1H), 4.919 (d, 2H), 2.919 (d, 3H), 2.558 (t, 1H), 2.151 (s, 3H).

Compound 10: 10.194 (br s, 1H), 8.375 (d, 1H), 7.845 (d, 1H), 7.159 (s, 1H), 7.121-7.102 (m, 2H), 6.238 (br s, 1H), 2.896 (s, 3H), 2.044 (s, 3H).

Compound 11: 9.933 (br s, 1H), 8.388 (d, 1H), 7.849 (d, 1H), 7.319 (s, 1H), 7.263-7.197 (m, 2H), 6.355 (br s, 1H), 3.006 (d, 3H).

Compound 14: (DMSO-$d_6$) 10.456 (br s, 1H), 8.557 (d, 1H), 8.405 (d, 1H), 7.769-7.502 (m, 4H), 7.408 (s, 1H).

Compound 15: (DMSO-$d_6$) 10.366 (br s, 1H), 8.549 (d, 1H), 8.393 (d, 1H), 7.718 (br s, 1H), 7.448-7.365 (m, 4H), 2.163 (s, 3H).

Compound 18: 10.208 (br s, 1H), 8.383 (d, 1H), 7.853 (d, 1H), 7.252 (s, 1H), 7.106-7.084 (m, 2H), 6.411 (br s, 1H), 2.903 (d, 3H), 2.085 (s, 3H).

Compound 19: 10.000 (br s, 1H), 8.395 (d, 1H), 7.856 (d, 1H), 7.311 (s, 1H), 7.223-7.142 (m, 2H), 6.434 (br s, 1H), 2.885 (d, 3H).

Compound 22: 10.242 (br s, 1H), 8.386 (d, 1H), 7.853 (d, 1H), 7.225 (s, 1H), 7.188-7.158 (m, 2H), 6.159 (br s, 1H), 3.405 (q, 2H), 2.227 (s, 3H), 1.237 (t, 3H).

Compound 23: 10.328 (br s, 1H), 8.383 (d, 1H), 7.844 (d, 1H), 7.369 (s, 1H), 7.096-7.08 (m, 2H), 6.026 (br s, 1H), 4.158 (m, 1H), 2.089 (s, 3H), 1.137 (d, 6H).

Compound 24: 10.194 (br s, 1H), 8.394 (d, 1H), 7.849 (d, 1H), 7.347 (s, 1H), 7.143-7.074 (m, 2H), 6.383 (br s, 1H), 2.803-2.768 (m, 1H), 2.163 (s, 3H), 0.900-0.834 (m, 2H), 0.548-0.494 (m, 2H).

Compound 25: 10.278 (br s, 1H), 8.383 (d, 1H), 7.837 (d, 1H), 7.354 (s, 1H), 7.115-7.082 (m, 2H), 6.095 (br s, 1H), 3.810 (m, 1H), 2.093 (s, 3H), 1.892-1.086 (m, 10H).

Compound 26: 10.000 (br s, 1H), 8.404 (d, 1H), 7.861 (d, 1H), 7.210-7.192 (m, 2H), 6.494 (br s, 1H), 4.147-4.108 (m, 2H), 2.264 (t, 1H), 2.143 (s, 3H).

Although the same Group atoms in the Periodic Table possess the similar chemical properties, however there are significant differences in their electronegativity and volume, which makes the different molecules show different liposolubility or mobility in the biological organisms such as insects, or plants. The suitable transportation properties of bioactive molecules play an important role in the biological efficacy. The transportation suitability of molecules is unpredictable, so it only can be discovered through extensively creative investigation.

Compared with the known compound such as 1-(3-chloro-5-bromopyridin-2-yl)-pyrazole carboxamide or 1-(3-chloro-2-pyridin-2-yl)-pyrazole carboxamide, the 1-substituted pyridyl-pyrazolyl amide compounds in the present invention possess surprisingly high insecticidal activity against the following insect: the order Lepidoptera such as Striped stem borer (*Chilo suppressalis* Walker), Yellow stem borer (*Scirpophaga incertulas* (Walker)), rice leaf roller (*Cniaphalocrosis medinalis* Guenee), corn borer (*Pyrausta nubilalis* (Hubern)), tobacco budwonn (*Heliothis virescens* Fabricius), oriental fruit moth (*Grapholitha molesta* (Busck)), diamondback moth (*Plutella xylostella* Linnaeus), beet armyworm (*Spodoptera exigua* Huibner), cluster caterpillar (*Spodoptera litura* Fabricius), corn earworm (*Helicoverpa zea* Boddie), fall armyworm (Mythimna separata Walker *Spodoptera frugiperda* J. E. Smith), cabbage looper (*Trichoplusiani* Huibner), etc.; the order Homoptera such as pea aphid (*Acyrthisiphon pisum* Harris), *Aphis craccivora* Koch (cowpea aphid), black bean aphid (*Aphis fabae* Scopoli), cotton aphid (*Aphis gossypii* Glover), apple aphid (*Aphis pomi* De Geer), green peach aphid (*Myzus peisicae* Sulzer), corn leaf aphid (*Rhopalosiphum maidis* Fitch), whitefly, leafhopper, lugens, rice delphacid (*Sogatodes orizicola* Muit), powder scale, ect.; the order Hemiptera such as chinch bug (*Blissus leucopterus leucopterus* Say), cotton lace bug (*Corythuca gossypii* Fabricius), tomato bug (*Cyropeltis modesta* Distant), southern green stink bug (*Nezara viridula* Linnacus), tice stink bug (*Oebalus pugnax* Fabricius), ect.; the order Thyasnoptera such as onion thrip (*Thrips tabaci* Lindeman), western flower thrip (*Frankliniella occidentalis* Pergande), soybean thrip (*Scirthothnips variabiis* Beach), ect.; the order Coleoptera such as Colorado potato beetle (*Leptinotarsa decemlineata* Say), Athous, ect.; the order Diptera such as fly, mosquito, ect.; The order Hymenoptera such as bee, ant ect. So, the present invention also provides the application of the general formula I compounds for controlling insects.

The 1-substituted pyridyl-pyrazolyl amide compounds in the present invention possess surprisingly high fungicidal activity, which can control the disease such as rice blast, *phytophthora infestans*, mould, powdery mildew, downy mildew, anthracnose, etc. So, the present invention also provides the application of general formula I compounds for combatting diseases.

The preparation of 1-substituted pyridyl-pyrazolyl amide compounds in the present invention is more convenient, more environmentally friendly. The preparation cost is lower. So it can be carried out to control the significant insects or diseases in agriculture, forestry or public health with the lower cost.

Another embodiment of the present invention includes the insecticidal or fungicidal compositions, in which the compounds of general formula I are active ingredients. The weight percentage of active ingredient(s) in the compositions is from 1% to 99%. There are also acceptable carriers in agriculture, forestry or public health in these compositions.

The compositions of the present invention can be used in the form of various formulations. Usually, the compounds of general formula I as the active ingredient can be dissolved in or dispersed in carriers or made to a formulation. So that they can be easily dispersed as an insecticide, or a fungicide such as a wettable powder or an emulsifiable concentrate etc. Therefore, in these compositions, at least a liquid or solid carrier is added, and usually suitable surfactant(s) can be added when needed.

Still also provided by the present invention are the application methods for controlling insects, which is to apply the compositions of the present invention to the growing loci of the insects as mentioned above. The suitably effective dosage of the compounds of the present invention is usually within a range of 10 g/ha to 1000 g/ha, preferably from 20 g/ha to 500 g/ha.

Also provided by the present invention are the application methods of controlling diseases, which is to apply the compositions of the present invention to the growing loci of the diseases as above mentioned. The suitably effective dosage of the compounds of the present invention is usually within a range of from 10 g/ha to 1000 g/ha, preferably from 20 g/ha to 500 g/ha.

For some applications, one or more other fungicides, insecticides, herbicides, plant growth regulators or fertilizer can be added into the insecticidal or fungicidal compositions of the present invention to make additional merits and effects.

It shall be noted that variations and changes are permitted within the claimed scopes in the present invention.

DESCRIPTION OF THE INVENTION IN DETAIL

The following synthesis examples and results of biological tests are used to further illustrate the present invention, but not to limit it.

Synthesis Examples

Example 1

Synthesis of Compound 1

(1) Synthesis of methyl 2,4-dioxopentanoate

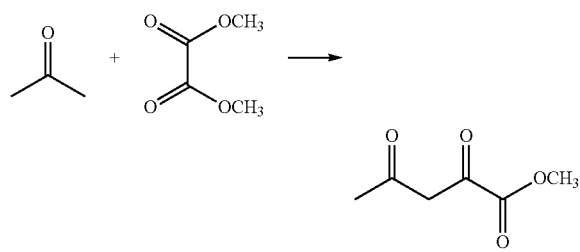

To a 500 mL flask, 25% sodium methoxide of methanol solution (43.20 g, 0.200 mol), methanol (200 mL) were added, the mixture of dimethyl oxalate (23.60 g, 0.200 mol) and acetone (11.60 g, 0.200 mol) were added dropwise at ice-salt bath. The reaction mixture was stirred for 8 hours at 0~5° C. The reaction mixture was poured into 200 mL water and extracted with ethyl acetate (150 mL) to remove organic impurity. The aqueous solution was acidified with concentrated hydrochloric acid to pH of 2~3 and extracted with ethyl acetate (3×200 mL). The organic layer was washed with water (150 mL), and saturated brine (150 mL), dried over anhydrous magnesium sulfate and concentrated to give the product (25.9 g) as yellow oil in 90% yield. $^1$H NMR (300 MHz, CDCl$_3$): 6.396 (s, 1H, enol isomer), 3.906 (s, 3H), 2.279 (s, 3H).

(2) Synthesis of 3,5-dichloro-2-hydrazinylpyridine

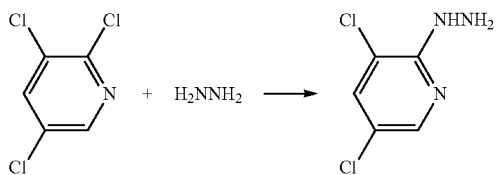

To a 500 mL flask, 2,3,5-trichloropyridine (20.00 g, 0.110 mol), 80% hydrazine (34.30 g, 0.550 mol) and dioxane (200 mL) were added sequentially. The reaction mixture was heated to reflux for 20 hours. Then the reaction mixture was cooled down to room temperature overnight and white crystal was precipitated. The white crystal was isolated via filtration and dried to give the product (14.0 g) as a white solid in 72% yield. Melting point: 187-189° C. $^1$H NMR (300 MHz, DMSO-d$_6$): 8.123 (d, 1H), 7.849 (d, 1H).

(3) Synthesis of methyl 1-(3,5-dichloropyridin-2-yl)-3-methyl-1H-pyrazole-5-carboxylate

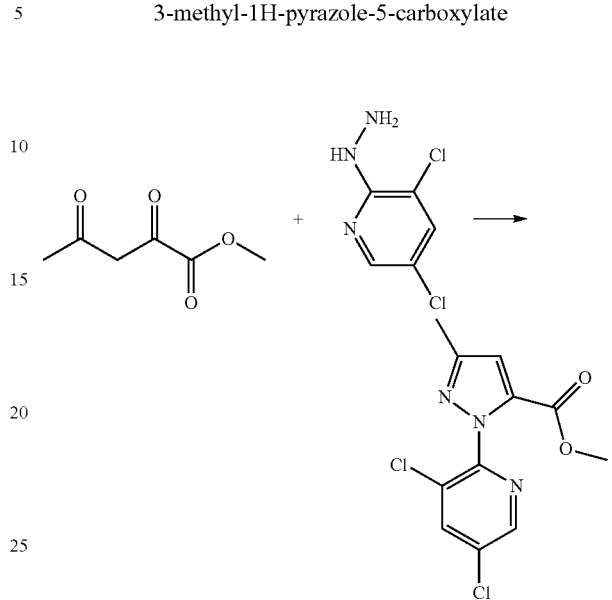

To a 100 mL flask, methyl 2,4-dioxopentanoate (2.88 g, 0.020 mol), tetrahydrofuran (15 mL), acetic acid (30 mL), and 3,5-dichloro-2-hydrazinylpyridine (3.56 g, 0.020 mol) were added sequentially. The reaction mixture was heated to reflux for 2 hours and then the mixture was concentrated by rotary evaporator. Then ethyl acetate (150 mL) and water (100 mL) was added, the organic layer was washed with saturated sodium bicarbonate solution (100 mL) and saturated brine (100 mL), dried over anhydrous magnesium sulfate and concentrated by rotary evaporator. The residue was purified by silica gel column chromatography (Fluent: ethyl acetate/petroleum ether=1/5) to give the product (2.9 g) as a white solid in 50% yield. Melting point: 97-98° C. $^1$H NMR (300 MHz, CDCl$_3$): 8.432 (d, 1H), 7.888 (d, 1H), 6.802 (s, 1H), 3.760 (s, 3H), 2.370 (s, 3H).

(4) Synthesis of 1-(3,5-dichloropyridin-2-yl)-3-methyl-1H-pyrazole-5-carboxylic acid

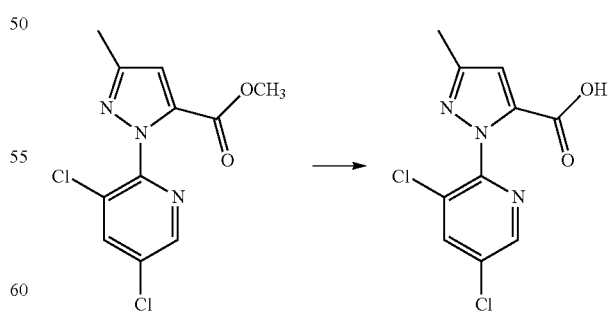

To a 100 mL flask, methyl 1-(3,5-dichloropyridin-2-yl)-3-methyl-1H-pyrazole-5-carboxylate (1.00 g, 3.49 mmol), tetrahydrofuran (10 mL), water (10 mL) and sodium hydroxide (0.14 g, 3.49 mmol) were added sequentially. After being stirred for 40 minutes at room temperature, all of the starting materials had disappeared. Then water (50 mL) was added. The mixture was extracted with ethyl acetate (30 mL) and the aqueous layer was acidified with concentrated hydrochloric acid to pH of 2~3, and extracted with ethyl acetate (3×80 mL), the organic layer was washed with saturated brine (100 mL), dried over anhydrous magnesium sulfate and concentrated by rotary evaporator to give the product (0.91 g) as a white solid in 96% yield. Melting point: 227-228° C.

$^1$H NMR (300 MHz, CDCl$_3$): 8.448 (s, 1H), 7.908 (s, 1H), 6.901 (s, 1H), 2.400 (s, 3H).

(5) Synthesis of 1-(3,5-dichloropyridin-2-yl)-3-methyl-1H-pyrazole-5-carbonyl chloride

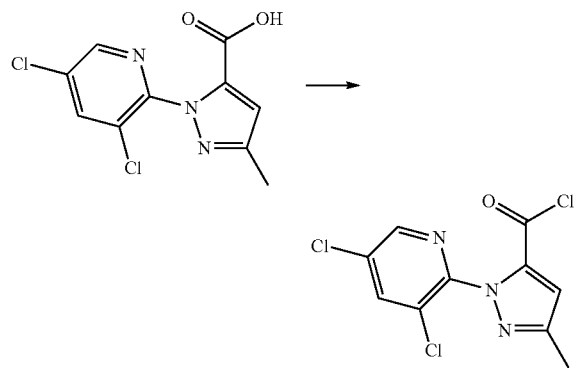

To a 100 mL flask, 1-(3,5-dichloropyridin-2-yl)-3-methyl-1H-pyrazole-5-carboxylic acid (0.37 g, 1.38 mmol), dichloromethane (10 mL) and oxalyl dichloride (0.35 g, 2.20 mmol) were added. After a drop of N,N-dimethyl formamide was added, a large number of gas was released. After being stirred for overnight at room temperature, the reaction mixture was concentrated under reduced pressure. Then 10 mL toluene was added, and the mixture was concentrated again under reduced pressure to give the product (0.40 g) as yellow oil in 100% yield.

(6) Synthesis of Compound 1

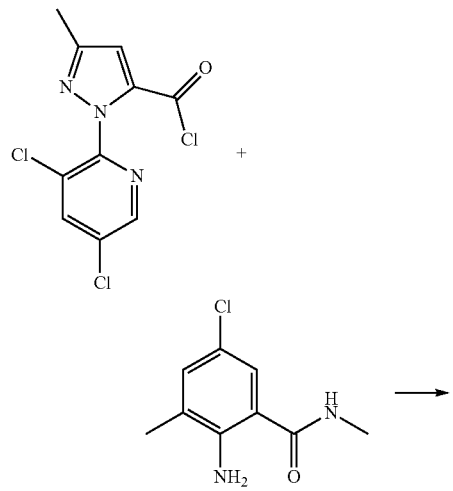

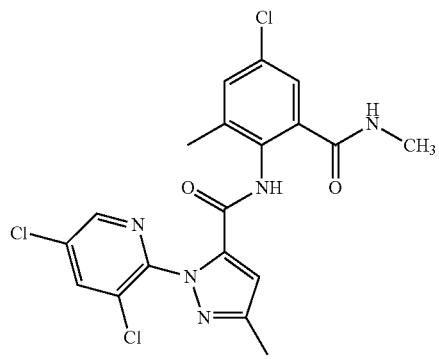

To a 100 mL, flask, 2-amino-5-chloro-N, 3-dimethylbenzamide (0.27 g, 1.38 mmol, prepared according to US2005075372), dichloromethane (5 mL) and triethylamine (0.14, 1.38 mmol) were added. Then the solution of 1-(3,5-dichloropyridin-2-yl)-3-methyl-1H-pyrazole-5-carbonyl chloride (0.40 g, 1.37 mmol) in dichloromethane (5 mL) were added dropwise. The reaction mixture was stirred for 4 hours at room temperature. Then the reaction mixture was poured into water (50 mL), and extracted with ethyl acetate (3×100 mL). The organic layer was washed with water and saturated brine, dried over anhydrous magnesium sulfate and concentrated by rotary evaporator. The residue was purified by silica gel column chromatography (Fluent: ethyl acetate/petroleum ether=1/5) to give the compound 1 (0.41 g) as a white solid in 66% yield.

Example 2

Synthesis of Compound 3

(1) Synthesis of 3,5-dichloro-2-hydrazinylpyridine

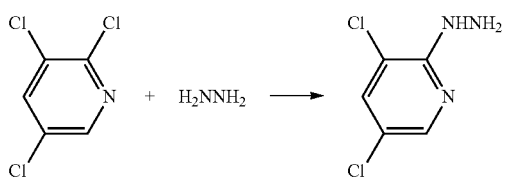

To a 500 mL flask, 2,3,5-trichloropyridine (20.00 g, 0.110 mol), 80% hydrazine (34.30 g, 0.550 mol) and dioxane (200 mL) were added sequentially. The reaction mixture was heated to reflux for 20 hours. Then the reaction mixture was cooled down to room temperature overnight and white crystal was precipitated. The white crystal was isolated via filtration and dried to give the product (14.0 g) as a white solid in 72% yield. Melting point: 187-189° C. $^1$H NMR (300 MHz, DMSO-d$_6$): 8.123 (d, 1H), 7.849 (d, 1H).

(2) Synthesis of 3,5-dichloro-2-(5-(furan-2-yl)-3-(trifluoromethyl)-1H-pyrazol-1-yl)pyridine

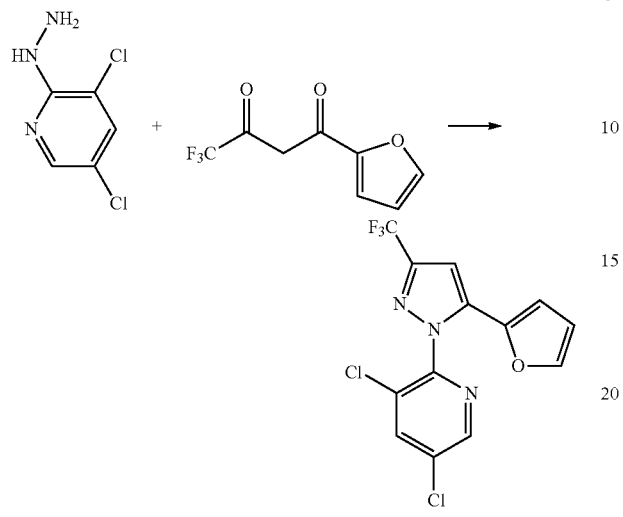

To a 250 mL flask, 4,4,4-trifluoro-1-(furan-2-yl)butane-1,3-dione (5.50 g, 26.7 mmol), 3,5-dichloro-2-hydrazinylpyridine (4.75 g, 26.7 mmol) and glacial acetic acid (100 mL) were added. The reaction mixture was heated to reflux. When the reaction completed, the reaction mixture was concentrated by rotary evaporator. Then ethyl acetate (300 mL) and water (150 mL) was added, the organic extracts were washed with saturated sodium bicarbonate solution (150 mL) and brine (150 mL) in sequence, dried over anhydrous magnesium sulfate and concentrated by rotary evaporator. The residue was purified by silica gel column chromatography (Fluent: ethyl acetate/petroleum ether=1/5) to give the product (5.66 g) as a yellow oil in 61% yield. ¹H NMR (300 MHz, CDCl₃): 8.514 (d, 1H), 7.974 (d, 1H), 7.362 (d, 1H), 6.917 (s, 1H), 6.388 (dd, 1H), 6.148 (d, 1H).

(3) Synthesis of 1-(3,5-dichloropyridin-2-yl)-3-(trifluoromethyl)-1H-pyrazole-5-carboxylic acid

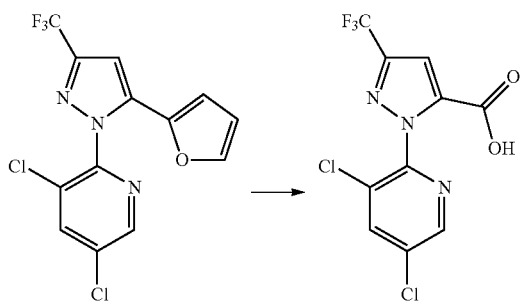 [SMILES: FC(F)(F)c1cc(-c2ccco2)n(-c2ncc(Cl)cc2Cl)n1 ; O=C(O)c1cc(C(F)(F)F)nn1-c1ncc(Cl)cc1Cl]

To a 100 mL flask, 3,5-dichloro-2-(5-(furan-2-yl)-3-(trifluoromethyl)-1H-pyrazol-1-yl)pyridine (1.47 g, 4.22 mmol), acetone (10 mL) and a solution (10 mL) of potassium permanganate (3.33 g, 21.1 mmol) in water were added. The reaction mixture was heated to 65° C. for 4 hours and cooled to room temperature, then isolated via filtration, a cake is obtained. The cake was washed with hot solution of potassium hydroxide. To the filtrate was added ethyl acetate (80 mL), water (100 mL) and partitioned. The aqueous layer was acidified with concentrated hydrochloric acid to pH of 2-3, and extracted with ethyl acetate (200 mL). The organic extracts were washed with saturated brine (100 mL), dried over anhydrous magnesium sulfate and concentrated by rotary evaporator to give the product (0.80 g) as yellow oil in 58% yield.

¹H NMR (300 MHz, CDCl₃): 8.480 (d, 1H), 7.969 (d, 1H), 7.345 (s, 1H).

(4) Synthesis of 1-(3,5-dichloropyridin-2-yl)-3-(trifluoromethyl)-1H-pyrazole-5-carbonyl chloride

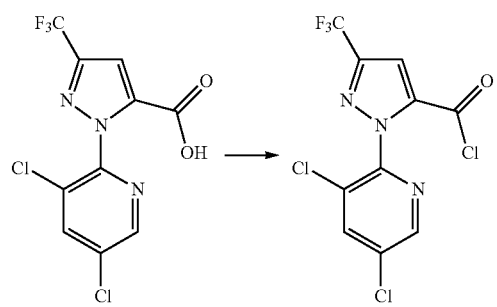 [SMILES: O=C(O)c1cc(C(F)(F)F)nn1-c1ncc(Cl)cc1Cl ; O=C(Cl)c1cc(C(F)(F)F)nn1-c1ncc(Cl)cc1Cl]

To a 100 mL flask, 1-(3,5-dichloropyridin-2-yl)-3-(trifluoromethyl)-1H-pyrazole-5-carboxylic acid (0.40 g, 1.22 mmol), dichloromethane (10 mL) and oxalyl dichloride (0.31 g, 2.44 mmol) were added sequentially. After five drops of N,N-dimethyl formamide were added, a large amount of gas was released. After being stirred for 8 hours at room temperature, the reaction mixture was concentrated under reduced pressure. Then toluene (30 mL) was added, and was concentrated again under vacuum to give the product (0.42 g) as yellow solid in 100% yield.

(5) Synthesis of Compound 3

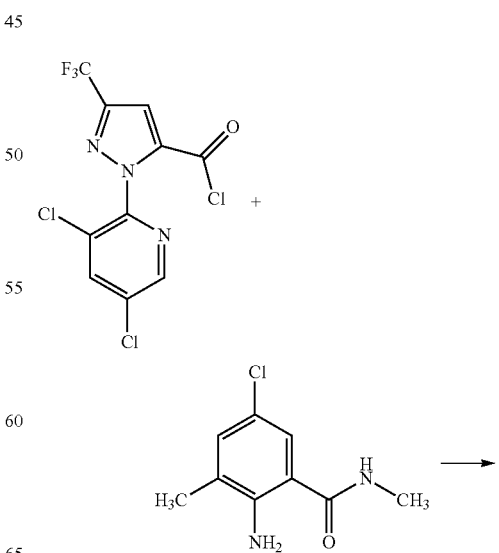

-continued

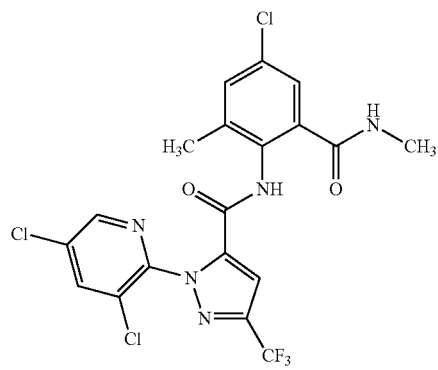

To a 100 mL flask, 2-amino-5-chloro-N,3-dimethylbenzamide (0.24 g, 1.22 mmol), dichloromethane (20 mL), 1-(3,5-dichloropyridin-2-yl)-3-(trifluoromethyl)-1H-pyrazole-5-carbonyl chloride (0.42 g, 1.22 mmol) and triethylamine (0.12 g, 1.22 mmol) were added sequentially. The reaction mixture was stirred for 3 hours at room temperature. The reaction mixture was poured into water (100 mL) and extracted with ethyl acetate (2×100 mL). The organic layer was washed with saturated sodium carbonate solution and saturated brine, dried over anhydrous magnesium sulfate and concentrated. The residue was purified by silica gel column chromatography to give the compound 3 (0.50 g) as a white solid in 81% yield.

Example 3

Synthesis of Compound 9

(1) Synthesis of 3,5-dichloro-2-hydrazinylpyridine

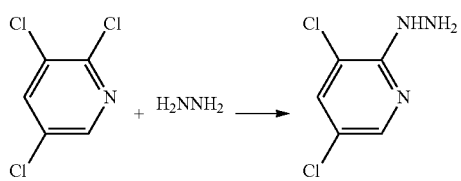

To a 500 mL flask, 2,3,5-trichloropyridine (20.00 g, 0.110 mol), 80% hydrazine (34.30 g, 0.550 mol) and dioxane (200 mL) were added sequentially. The reaction mixture was heated to reflux for 20 hours. Then the reaction mixture was cooled down to room temperature overnight and white crystal was precipitated. The white crystal was isolated via filtration and dried to give the product (14.0 g) as a white solid in 72% yield. Melting point: 187-189° C.

$^1$H NMR (300 MHz, DMSO-d$_6$): 8.123 (d, 1H), 7.849 (d, 1H).

(2) Synthesis of ethyl 2-(3,5-dichloropyridin-2-yl)-5-oxopyrazolidine-3-carboxylate

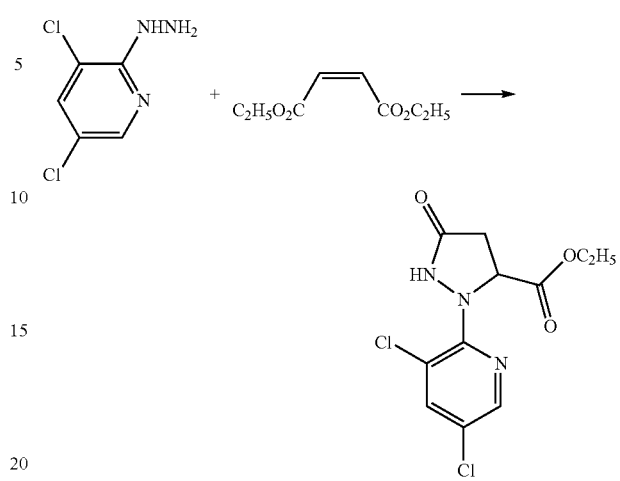

To a 500 mL flask, 300 mL anhydrous ethanol, sodium ethoxide (4.1 g, 61 mmol) and 3,5-dichloro-2-hydrazinylpyridine (10.00 g, 56 mmol) were added. The reaction mixture was heated to reflux for 5 minutes. Diethyl maleate (10.64 g, 61.0 mmol) was added dropwise and heated to reflux for 10 minutes. After being cooled to 65° C., the reaction mixture was neutralized with glacial acetic acid (13 g, 224 mmol) and diluted with 300 mL water. The mixture was cooled down to room temperature and the a precipitate formed. The solid was isolated via filtration, washed with 40% aqueous solution of ethanol (3×50 mL) and dried to give the product (8.00 g) as an orange solid in 47% yield. Melting point: 105-108° C.

$^1$H NMR (300 MHz, CDCl$_3$): 8.146 (q, 1H), 7.658 (q, 1H), 5.073 (dd, 1H), 4.241 (q, 2H), 3.029 (dd, 1H), 2.721 (dd, 1H), 1.258 (t, 3H).

(3) Synthesis of ethyl 1-(3,5-dichloropyridin-2-yl)-3-hydroxy-1H-pyrazole-5-carboxylate

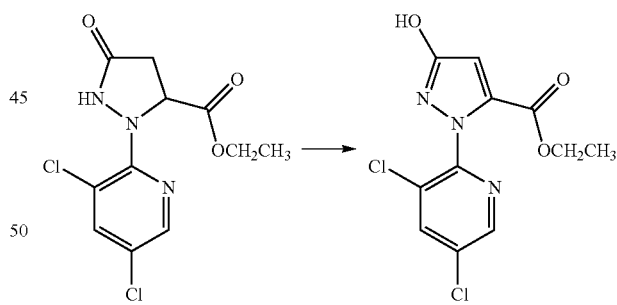

To a 100 mL flask, ethyl 2-(3,5-dichloropyridin-2-yl)-5-oxopyrazolidine-3-carboxylate (4.00 g, 13.15 mmol), acetonitrile (50 mL) and 98% sulfuric acid (2.63 g, 26 mmol) were added. The mixture was stirred for 10 minutes, and then potassium persulfate (5.69 g, 21.04 mmol) was added. The reaction mixture was heated to reflux for 5 hours. The warm (50-65° C.) reaction mixture was filtered, a cake is obtained after filtration. The cake was washed with acetonitrile (10 mL). The filtrate was concentrated to about 10 mL on rotary evaporator. Then water (50 mL) was added. The solid product was isolated by filtration, washed with 25% aqueous solution of acetonitrile (3×15 mL) and dried to give the product (3.0 g) as an orange solid in 76% yield. Melting point: 164-167° C.

$^1$H NMR (300 MHz, CDCl$_3$): 8.445 (d, 1H), 7.912 (d, 1H), 6.546 (s, 1H), 4.262 (q, 2H), 1.236 (t, 3H).

(4) Synthesis of ethyl 1-(3,5-dichloropyridin-2-yl)-3-(prop-2-ynyloxy)-1H-pyrazole-5-carboxylate

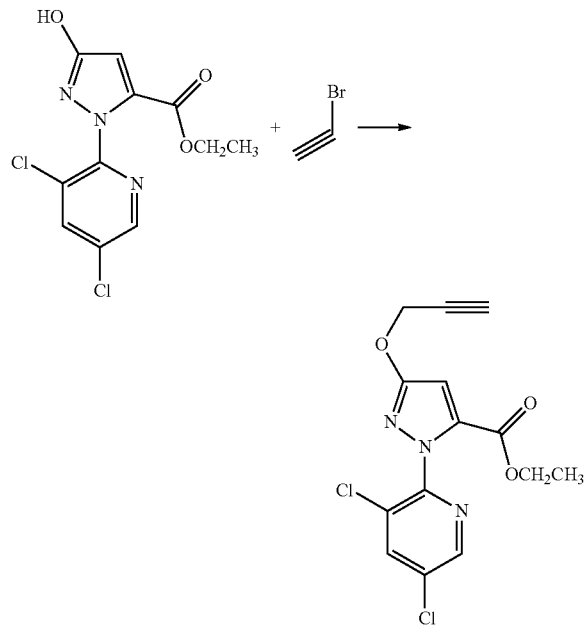

To a 100 mL flask, ethyl 1-(3,5-dichloropyridin-2-yl)-3-hydroxy-1H-pyrazole-5-carboxylate (0.7 g, 2.32 mmol), acetonitrile (10 mL), potassium carbonate (0.32 g, 2.32 mmol) and 3-bromoprop-1-yne (0.27 g, 2.32 mmol) were added sequentially. The reaction mixture was heated to 60° C. for 2 hours. Then the reaction mixture was poured into water (100 mL), extracted with ethyl acetate (2×100 mL). The organic layer was washed with saturated sodium carbonate solution (80 mL) and saturated brine (80 mL), dried over anhydrous magnesium sulfate and concentrated. The residue was purified by silica gel column chromatography to give the compound (0.30 g) as yellow oil in 38% yield.
$^1$H NMR (300 MHz, CDCl$_3$): 8.445 (d, 1H), 7.902 (d, 1H), 6.498 (s, 1H), 4.896 (d, 2H), 4.240 (q, 2H), 2.547 (t, 1H), 1.260 (t, 3H).

(5) Synthesis of 1-(3,5-dichloropyridin-2-yl)-3-(prop-2-ynyloxy)-1H-pyrazole-5-carboxylic acid

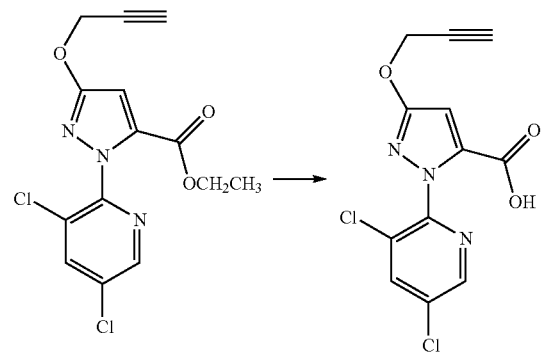 [SMILES: C#CCOc1cc(C(=O)OCC)n(-c2ncc(Cl)cc2Cl)n1 ; C#CCOc1cc(C(=O)O)n(-c2ncc(Cl)cc2Cl)n1]

To a 100 mL flask, ethyl 1-(3,5-dichloropyridin-2-yl)-3-(prop-2-ynyloxy)-1H-pyrazole-5-carboxylate (0.3 g, 0.88 mmol), methanol (10 mL), water (10 mL) and sodium hydroxide (0.04 g, 0.88 mmol) were added. The reaction mixture was stirred at room temperature for 1 hour. When reacted completely, water (40 mL) was added. The water (40 mL), ether (50 mL) were added and partitioned, acidified with concentrated hydrochloric acid to pH of 4, extracted with ethyl acetate (150 mL). The organic layer was washed with saturated brine (50 mL), dried over anhydrous magnesium sulfate and concentrated at reduced pressure to give the product (0.27 g) as slight yellow solid in 73% yield. Melting point: 151-157° C.
$^1$H NMR (300 MHz, CDCl$_3$): 8.429 (d, 1H), 7.900 (d, 1H), 6.563 (s, 1H), 4.882 (s, 2H), 2.550 (s, 1H).

(6) Synthesis of 1-(3,5-dichloropyridin-2-yl)-3-(prop-2-ynyloxy)-1H-pyrazole-5-carbonyl chloride

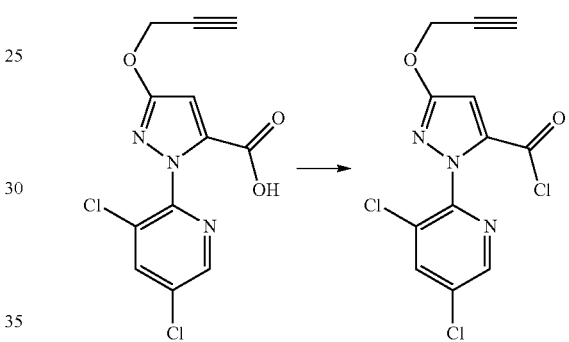

To a 100 mL flask, 1-(3,5-dichloropyridin-2-yl)-3-(prop-2-ynyloxy)-1H-pyrazole-5-carboxylic acid (0.2 g, 0.64 mmol), dichloromethane (10 mL) and oxalyl dichloride (0.16 g, 1.2 mmol) were added. After five drops of N,N-dimethyl formamide were added, a large number of gas was released. After being stirred for 8 hours at room temperature, the reaction mixture was evaporated to dryness at reduced pressure. Then 100 mL toluene was added, and the reaction mixture was concentrated again under reduced pressure to give the product (0.21 g) as yellow solid in 100% yield.

(7) Synthesis of Compound 9

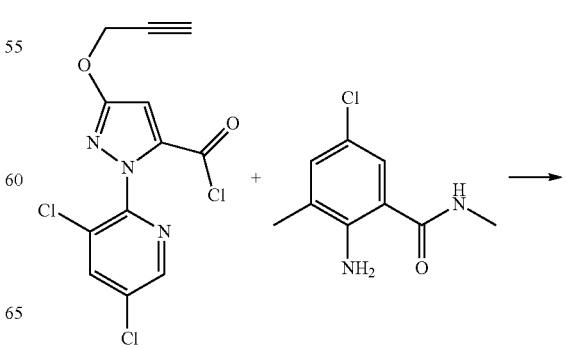

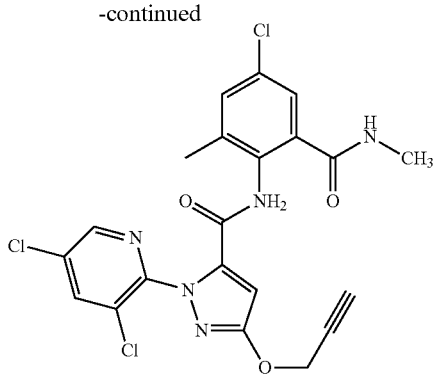

To a 100 mL flask, 2-amino-5-chloro-N,3-dimethylbenzamide (0.12 g, 0.6 mmol), dichloromethane (20 mL), 1-(3,5-dichloropyridin-2-yl)-3-(prop-2-ynyloxy)-1H-pyrazole-5-carbonyl chloride (0.2 g, 0.6 mmol) and triethylamine (0.06 g, 0.6 mmol) were added. After being stirred for 3 hours at room temperature, the reaction mixture was poured into water (100 mL) and extracted with ethyl acetate (2×100 mL). The organic layer was washed with saturated sodium carbonate solution and saturated brine, dried over anhydrous magnesium sulfate and concentrated. The residue was purified by silica gel column chromatography to give the compound 9 (0.24 g) as a white solid in 81% yield.

Example 4

Synthesis of Compound 18

(1) Synthesis of ethyl 3-bromo-1-(3,5-dichloropyridin-2-yl)-4,5-dihydro-1H-pyrazole-5-carboxylate

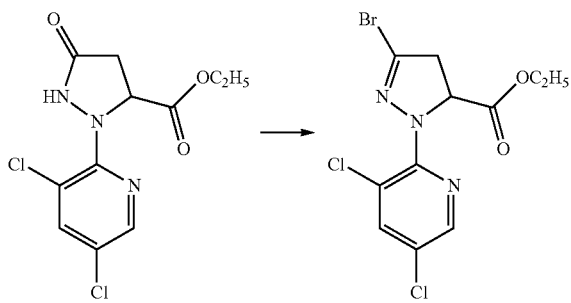 [SMILES: CCOC(=O)C1CC(=O)NN1c1ncc(Cl)cc1Cl ; CCOC(=O)C1CC(Br)=NN1c1ncc(Cl)cc1Cl]

To a 250 mL flask, acetonitrile (65 mL), ethyl 2-(3,5-dichloropyridin-2-yl)-5-oxopyrazolidine-3-carboxylate (3.0 g, 9.8 mmol, the product of Step (3), Example 3) and phosphoryl bromide (2.8 g, 9.8 mmol) were added. The reaction mixture was heated to reflux for 2 hours. The reaction mixture was distilled to remove 30 mL solvent and added to the mixture of sodium carbonate (10 g, 120 mmol) and water (40 mL). The mixture was stirred for 20 minutes until no gas released. The reaction mixture was diluted with dichloromethane (100 mL), stirred for 50 minutes and extracted with dichloromethane (3×100 mL). The organic layer was washed with water, dried over anhydrous magnesium sulfate, and concentrated under vacuum to give the product (2.4 g) as amber oil in 67% yield. $^1$H NMR (300 MHz, CDCl$_3$): 8.027 (d, 1H), 7.673 (d, 1H), 5.201 (dd, 1H), 4.202 (q, 2H), 3.464 (dd, 1H), 3.248 (dd, 1H), 1.223 (t, 3H).

(2) Synthesis of ethyl 3-bromo-1-(3,5-dichloropyridin-2-yl)-1H-pyrazole-5-carboxylate

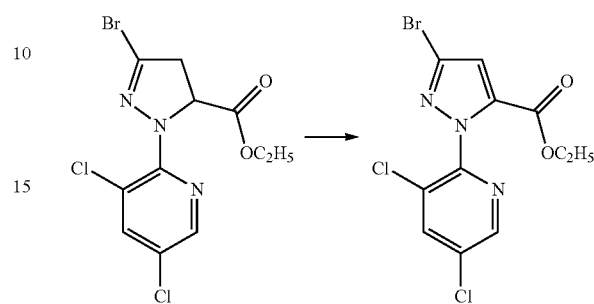

To a 100 mL flask, ethyl 3-bromo-1-(3,5-dichloropyridin-2-yl)-4,5-dihydro-1H-pyrazole-5-carboxylate (2.0 g, 5.4 mmol), acetonitrile (10 mL) and 98% sulfuric acid (1.1 g, 10.9 mmol) were added. The mixture was stirred for a few minutes, and then potassium persulfate (2.4 g, 8.7 mmol) was added. The reaction mixture was heated to reflux for 5 hours. The warm (50-65° C.) reaction mixture was filtered, a cake is obtained. The cake was washed by acetonitrile (10 mL). The filtrate was concentrated to about 10 mL on rotary evaporator. Then water (50 mL) was added. The solid product was isolated by filtration, washed with 25% aqueous solution of acetonitrile (3×15 mL) and dried to give the product (1.6 g) as orange solid in 80% yield.
$^1$H NMR (300 MHz, CDCl$_3$): 8.461 (d, 1H), 7.933 (d, 1H), 7.035 (s, 1H), 4.263 (q, 2H), 1.262 (t, 3H).

(3) Synthesis of 3-bromo-1-(3,5-dichloropyridin-2-yl)-1H-pyrazole-5-carboxylic acid

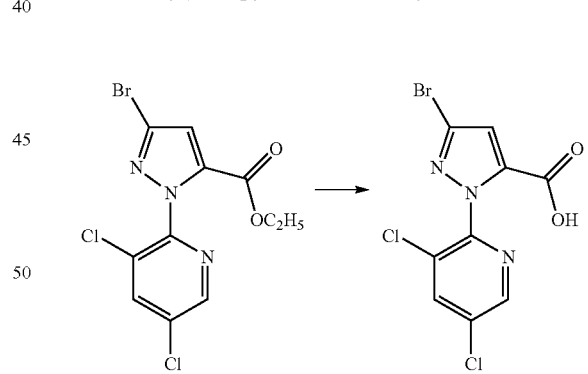

To a 100 mL flask, ethyl 3-bromo-1-(3,5-dichloropyridin-2-yl)-1H-pyrazole-5-carboxylate (2.0 g, 5.5 mmol), methanol (10 mL), water (10 mL) and sodium hydroxide (0.3 g, 5.5 mmol) were added. After being stirred at room temperature for 1 hour, the mixture reacted completely. The reaction mixture was concentrated by rotary evaporator to about 10 mL as a dark brown solution. Then water (40 mL) was added into the dark brown solution. The aqueous solution was extracted with ethyl ether (50 mL) and acidified with concentrated hydrochloric acid to pH of 4. The precipitate was isolated by filtration, washed with water (2×50 mL) and dried to give the product (0.97 g) as white solid in 48% yield.

¹H NMR (300 MHz, DMSO-d₆): 8.641 (d, 1H), 8.529 (d, 1H), 7.186 (s, 1H).

(4) Synthesis of 3-bromo-1-(3,5-dichloropyridin-2-yl)-1H-pyrazole-5-carbonyl chloride

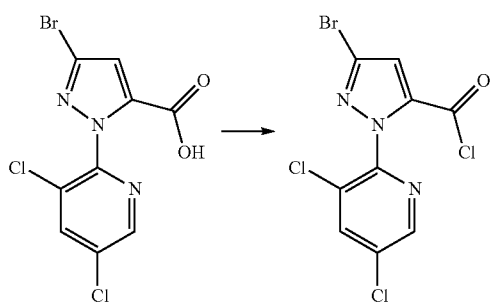 [SMILES: O=C(O)c1cc(Br)nn1-c1ncc(Cl)cc1Cl ; O=C(Cl)c1cc(Br)nn1-c1ncc(Cl)cc1Cl]

To a 100 mL flask, 3-bromo-1-(3,5-dichloropyridin-2-yl)-1H-pyrazole-5-carboxylic acid (0.4 g, 1.2 mmol), dichloromethane (10 mL) and oxalyl dichloride (0.31 g, 2.4 mmol) were added. After five drops of N,N-dimethyl formamide was added, a large number of gas was released. After being stirred for 8 hours at room temperature, the reaction mixture was evaporated to dryness at reduced pressure. Then toluene (100 mL) was added, and the reaction mixture was concentrated again under vacuum to give the product (0.42 g) as green solid in 100% yield.

(5) Synthesis of Compound 18

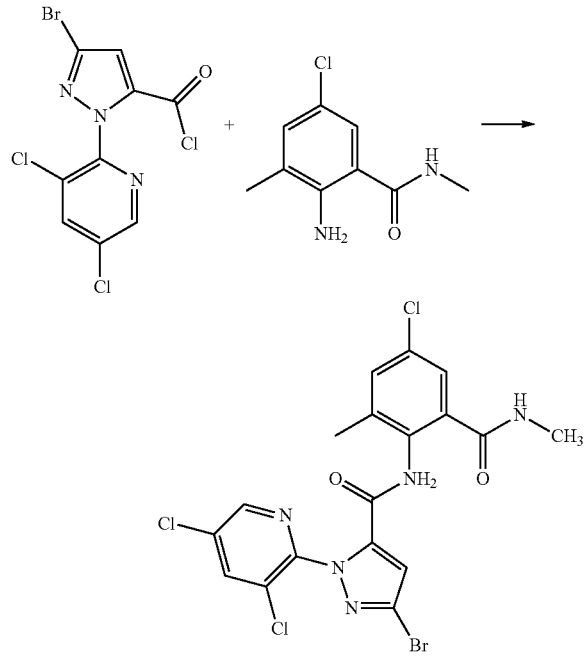

To a 100 ml, flask, 2-amino-5-chloro-N,3-dimethylbenzamide (0.34 g, 1.7 mmol), dichloromethane (20 mL), 3-bromo-1-(3,5-dichloropyridin-2-yl)-1H-pyrazole-5-carbonyl chloride (0.60 g, 1.7 mmol) and triethylamine (0.17 g, 1.7 mmol) were added. The reaction mixture was stirred for 3 hours at room temperature, and then poured into water (100 mL), extracted with ethyl acetate (2×100 mL), washed with saturated sodium carbonate solution and saturated brine, dried over anhydrous magnesium sulfate and concentrated. The residue was purified by silica gel column chromatography (Fluent: ethyl acetate/petroleum ether=1/2) to give the compound 18 (0.21 g) as white solid in 24% yield.

Example 5

Synthesis of Compound 19

(1) Synthesis of 2-(3-bromo-1-(3,5-dichloropyridin-2-yl)-1H-pyrazol-5-yl)-6,8-dichloro-4H-benzo[d][1,3]oxazin-4-one

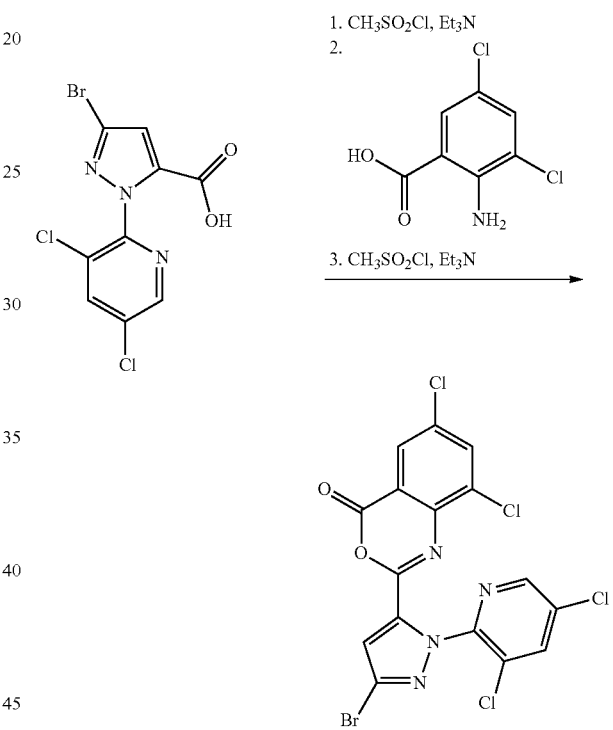

To a 150 mL flask, methanesulfonyl chloride (1.1 g, 9.8 mmol), acetonitrile (20 mL) was added. Then the mixture of 3-bromo-1-(3,5-dichloropyridin-2-yl)-1H-pyrazole-5-carboxylic acid (3.0 g, 8.9 mmol, the product of step (3), example 4) and triethylamine (0.89 g, 8.9 mmol) in acetonitrile (30 mL) were added dropwise in 10 minutes at room temperature. The mixture was stirred for 1 hour. 2-Amino-3,5-dichlorobenzoic acid (1.6 g, 17 mmol) was added, and the reaction mixture turned into reddish brown. After being stirred for 30 minutes, the solution of triethylamine (1.8 g, 17 mmol) in acetonitrile (10 mL) was added dropwise and yellow solid precipitated. The mixture was stirred for 1 hour, another solution of methanesulfonyl chloride (1.1 g, 9.8 mmol) in acetonitrile (10 mL) was added. The reaction mixture turned into yellow and solid was precipitated. After being stirred for 1 hour, another solution of triethylamine (0.89 g, 8.9 mmol) in acetonitrile (4 mL) was added. Then the reaction mixture was stirred for overnight at room temperature. The reaction mixture was poured into water (100 mL), extracted with ethyl acetate (2×100 mL), washed with saturated sodium carbonate solution and saturated brine, dried over anhydrous magnesium sulfate and concentrated. The residue was purified by silica gel column chromatography (Fluent: ethyl acetate/petroleum ether=1/2) to give the product (2.0 g) as a yellow solid in 45% yield.

(2) Synthesis of Compound 19

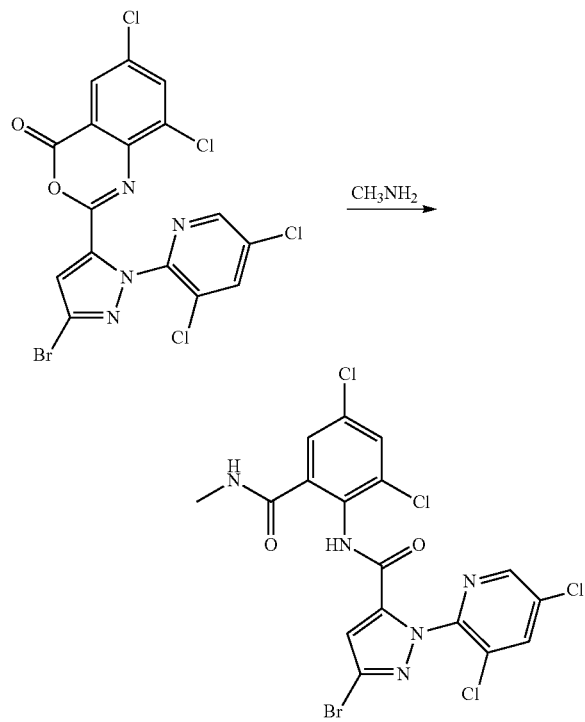 [SMILES: O=c1oc(-c2cc(Br)nn2-c2ncc(Cl)cc2Cl)nc2c(Cl)cc(Cl)cc12 ; "CH3NH2" ; CNC(=O)c1cc(Cl)cc(Cl)c1NC(=O)c1cc(Br)nn1-c1ncc(Cl)cc1Cl]

To a 100 mL flask, 2-(3-bromo-1-(3,5-dichloropyridin-2-yl)-1H-pyrazol-5-yl)-6,8-dichloro-4H-benzo[d][1,3]oxazin-4-one (0.3 g, 0.6 mmol), tetrahydrofuran (4 mL) were added. When all starting materials were dissolved, methylamine (0.09 g, 0.9 mmol, 30%) was added dropwise at room temperature. The mixture reacted completely after 30 minutes. The water was added and the mixture was extracted with ethyl acetate. The organic layer was washed with saturated brine, dried over anhydrous magnesium sulfate and concentrated to give the compound 19 (0.14 g) as a white solid in 43% yield.

Biological Test Examples

Example 6

Tests of Insecticidal Activity

According to the solubility of test compounds, the compounds are dissolved in acetone or dimethyl sulfoxide, and then diluted with 0.1% aqueous solution of Tween 80 to form 50 ml test liquid, the content of acetone or dimethyl sulfoxide in the total solution is not more than 10%.

Exp. 6.1 Test Against Beet Armyworm (*Laphygma exigua Hubner*)

The cabbage leaves were perforated to get 1 cm diameter leaf discs by the hole puncher. Certain concentrations of test compounds were sprayed on both sides of the discs at the spray volume of 0.5 ml by Airbrush. Eight test insects (third instar) were introduced on each treatment after drying. Each treatment repeated 3 times. The treated discs were placed in a chamber of 24° C., 60%-70% relative humidity, no light. After 96 h, the number of surviving insects was investigated and the mortality was calculated.

Among some of the testing compounds, the compounds 1, 3, 9, 15, 18, 19, 22, 26 exhibited mortality 90% or more against beet armyworm at 10 ppm.

Among some of the testing compounds, the compounds 3, 9, 18, 19, 22, 26 exhibited mortality 90% or more against beet armyworm at 1 ppm.

According to above method, compound 18, 19 and $KC_1$ (compound 833 in the patent US2005/0075372A1) were chosen to parallel activity test against beet armyworm. The two test results were listed in Table 3 and Table 4.

TABLE 3

Parallel test result of compounds 18, 19, and $KC_1$ against beet armyworm (mortality, %)

| Compounds | ppm 0.3 Mortality (%) |
|---|---|
| 18 | 50 |
| 19 | 87.5 |
| $KC_1$ | 0 |

TABLE 4

Parallel test result of compounds 18 and $KC_1$ against beet armyworm (mortality, %)

| | Concentration ppm | |
|---|---|---|
| Compounds | 0.6 Mortality (%) | 0.3 |
| 18 | 100 | 62 |
| $KC_1$ | 75.5 | 12.5 |

Exp. 6.2 Test Against Army Worm (*Mythimna separata*)

The middle part of fresh corn leaves were chosen and cut into 3 cm sects. The sects were dipped into the solution of certain concentration of test compounds for 10 seconds, dried and placed in 9 cm diameter Petri dish. Eight regular health insects (third instar) were introduced on each treatment. Each treatment was repeated for 4 times. The pure water was set as CK. The treated discs were placed in a chamber of 24° C., 60%-70% relative humidity and day light. After 72 h, the number of surviving insects was investigated and the mortality rates were calculated.

Among some of the testing compounds, the compounds 18, 19 exhibit mortality 90% or more against army worm at 0.4 ppm.

Exp. 6.3 Test Against Diamondback Moth (*Plutella xylostella*)

The leaves of cabbage grown in greenhouse were chosen, removed the surface waxy layer and perforated to get 2 cm diameter leaf discs by the hole puncher. The discs were dipped in a solution of certain concentrations of test compounds for 10 seconds, dried and placed in 9 cm diameter Petri dish. Eight regular health insects (third instar) were introduced on each treatment. Each treatment was repeated for 4 times. The pure water was set as CK. The treated discs were placed in a chamber of 24° C., 60%-70% relative humidity and day light. After 72 h, the number of surviving insects was investigated and the mortality was calculated.

Among some of the testing compounds, the compound 19 exhibit mortality more than 90% against Diamondback moth at 0.8 ppm.

Exp. 6.4 Test Against Striped Stem Borer (*Chilo suppressalis* (Walker))

The 6 well culture plates were chosen, 5 mL artificial feed was added into each well. After the feed solidified, 0.2 mL solution of certain concentrations of test compounds was added into per well with a continuous sampler and made the uniform film in the feed surface. Eight regular health insects (second instar) were introduced on each treatment after drying. Each treatment was repeated for 4 times. The pure water was set as CK. The treated discs were placed in a chamber of 24° C., 60%-70% relative humidity and day light. After 72 h, the number of surviving insects was investigated and the mortality was calculated.

Among some of the testing compounds, the compounds 18, 19 exhibit mortality 90% or more against striped stem borer at 10 ppm.

According to above method, compound 19 and $KC_2$ (compound 531 in the patent US2005/0075372A1) were choosen to parallel activity test against striped stem borer. The testing result was listed in table 5.

TABLE 5

Parallel test result of compounds 19 and $KC_2$ against striped stem borer (mortality, %)

| Compounds | Concentration ppm | |
|---|---|---|
| | 10 | 5 |
| | Mortality (%) | |
| 19 | 100 | 90 |
| $KC_2$ | 90 | 60 |

Exp. 6.5 Field Test Against Rice Leaf Folder (*Cnaphalocrocis medinalis* Guenee)

A certain concentrations of test compounds were sprayed on leaves at the time of hatching peak of rice leaf folder. Spay volume was 450 L/ha. The section area of rice was 32 m². Each treatment was repeated for 3 times. After 7d, the number of surviving insects was investigated and the mortality was calculated. The result was listed in table 6.

TABLE 6

Parallel test result of compounds 19 and $KC_2$ against rice leaf folder (mortality, %)

| Compounds | Dose (g/ha) | |
|---|---|---|
| | 60 | 30 |
| | Mortality (%) | |
| 19 | 63 | 56 |
| $KC_2$ | 52 | 34 |

Exp. 7 Tests of Fungicidal Activity

Exp. 7.1 Fungicidal Activity Test Against Tomato Late Blight In Vitro (*Phytophthora infestans*).

The melt AEA culture medium was cooled to 60-70° C., and calculated amount of the test compounds were added according to the designed concentration to prepare compound-containing culture medium, the final content of test compound was 25 ppm. After the medium cooled down sufficiently, tomato late blight pathogen of 0.5 cm diameter was inoculated and placed into the growth oven. The evaluation was performed after 10 days after inoculation. The measurement of the diameter of each colony was carried out and the rate of fungi inhibition was calculated.

The control efficiency of compound 1 against tomato late blight is more than 90%.

Exp. 7.2 Fungicidal Activity Test Against Cucumber Anthracnose In Vivo (*Colletotrichum lagenarium*, CA):

Select a uniformly growth of potted cucumber seedlings, neatly cut growing point and two mail leaves reserved. The testing compound solutions were sprayed at 400 ppm. Cucumber anthracnose spore suspension was inoculated at the second day after the treatment of the test materials, then placed in the artificial climate chamber (temperature: 22° C., relative humidity: >95%) to cultivate, and then placed into greenhouse to cultivate after 1 day. After 5 days the protection and control effect was investigated according to the blank control using visual assessment survey and recorded with 100% to 0, 100% is no disease, 0 indicated that the incidence level of the treatment was same with blank control.

The protective controlling effect of compound 1 against cucumber anthracnose is more than 90%.

What is claims is:

1. A 1-substituted pyridyl-pyrazolyl amide compound represented by formula I:

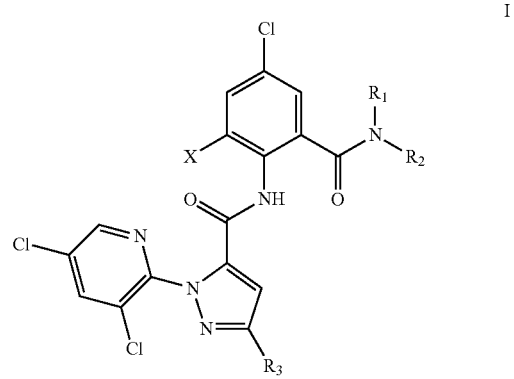

wherein:
$R_1$ is H;
$R_2$ is H or $CH_3$;
$R_3$ is Cl or Br; and
X is Cl or $CH_3$.

2. The compound according to claim 1, wherein:
$R_2$ is $CH_3$.

3. The compound according to claim 2, wherein:
$R_3$ is Br.

4. A method of controlling insects which comprises applying the compound according to claim 1 in an effective amount to the insects or to an area in which the insects are to be controlled.

5. An insecticidal composition which comprises a compound according to claim 1 and an acceptable carrier in agriculture, forestry or public health, in which the weight percentage of active ingredient(s) is in the range of 1%-99%.

6. A method for controlling insects, which comprises applying the composition of claim 5 to the insects or to an area in which the insects are to be controlled with effective dosage within a range of from 10 g/ha to 1000 g/ha.

* * * * *